United States Patent [19]

Mauro et al.

[11] Patent Number: 5,292,519
[45] Date of Patent: Mar. 8, 1994

[54] PROCESS FOR PRODUCING A PHARMACEUTICAL TABLET USING A HOMOZYGOUS WHITE STARCH

[75] Inventors: David J. Mauro, Dolton, Ill.; Frances L. Turnak, Hammond, Ind.

[73] Assignee: American Maize Technology, Inc., Dimmitt, Tex.

[21] Appl. No.: 866,421

[22] Filed: Apr. 10, 1992

[51] Int. Cl.$^5$ .................. A61K 9/48; A61K 47/00
[52] U.S. Cl. .................. 424/465; 514/778; 514/960; 514/961
[58] Field of Search .................. 514/778, 960, 961; 424/465

[56] References Cited

U.S. PATENT DOCUMENTS 5,139,809  8/1992  Wienan et al. .................. 426/578

FOREIGN PATENT DOCUMENTS 9215285  9/1992  PCT Int'l Appl. .

OTHER PUBLICATIONS

Gergelz et al; CA 115(12), 120090u (1991).
Bos et al, Pharm. Week 61. Sci. Ed. 9:274–282 (1987).
Nasipuri, et al, Smilers Chemist, "Pharm. Ind." 44:1288–1292 (12)(1982).

Primary Examiner—Frederick E. Waddell
Assistant Examiner—T. J. Criares
Attorney, Agent, or Firm—Lucas & Just

[57] ABSTRACT

The use of a starch obtained from a plant source that is homozygous in a white recessive gene, such as white common corn starch, has superior compression and ejection forces compared to commercial disintegrantants/binders. The starch derived from common corn containing the homozygous white recessive gene was also found to have comparable whiteness to commercial bleached corn starches used in tableting.

6 Claims, No Drawings

PROCESS FOR PRODUCING A PHARMACEUTICAL TABLET USING A HOMOZYGOUS WHITE STARCH

This invention relates to pharmaceutical tablets and, more specifically, to a method for producing a pharmaceutical tablet which readily disintegrates in water and in the gastrointestinal tract after being swallowed.

Tablets are used not only in the pharmaceutical field to provide a host with a drug dosage but also for diagnostic and analytical purposes to provide a host with a set amount of a reagent. The primary advantages of tablets is their ease of handling and simplicity of dosing. The tablet does not only contain the reagent or drug but also contains other ingredients which act as fillers, such as lactose, phosphates or the like; lubrication agents, such as talc, stearic acid, paraffin or the like; and disintegration agents such as carboxymethyl-cellulose, starch and the like. These disintegration agents act not only to promote disintegration, but also as a binder to hold the tablet together prior to ingestion by the host. Additionally, some tablets contain an effervescent agent which reacts with water to cause the tablet to disintegrate. Typical effervescent agents are sodium bicarbonate and citric or tartaric acid.

Normally, tablets are made using a tableting press in which the preblended components are compressed to form the tablet. This is normally a dry process. Additionally, wet granulation is also employed to form tablets. This wet process entails forming a stiff slurry of the ingredients, forming tablets out of the slurry, and drying the wet tablet. The major drawback to the wet process is that it cannot be used with compounds that are sensitive to moisture and heat.

In the wet or dry process, a certain amount of energy is expended in order to form the tablet. Energy is used not only to compress the ingredients into a tablet but also to eject or expel the tablet from the press once the tablet is formed. Although the amount of force or energy needed to both form the tablet and eject the formed tablet from the press is small on a per tablet basis, the energy is substantial given the large number of tablets that are manufactured over a period of time. A reduction in the amount of energy needed for production of a tablet translates into a cost savings to the tablet manufacturer and, if passed along, to the ultimate consumer.

The majority of the corn starches used to make tablets are bleached starches. The bleaching changes the yellow corn starch to a white color which is deemed more acceptable than yellow. Bleaching also controls microbial growth. Bleaching of corn starch also has the detrimental effect of introducing a chlorine-like flavor to the starch. This chlorine-like flavor, although undesirable, is deemed unavoidable if corn starch is used in the tablet formulation.

Additionally, because the bleaching is an additional step which is performed on the corn starch, it increases the cost of the starch used in the tablet.

There is a need in the pharmaceutical industry to reduce the cost of tablets as well as eliminate the poor taste associated with bleached corn starch.

It has now been discovered that a starch obtained from a plant that is homozygous in a white (w) recessive gene, when used in a tablet formulation, provides a tablet which readily disintegrates in water and in the gastrointestinal tract after swallowing by the host. It has also been found that a corn starch obtained from maize that is homozygous in the white recessive gene is of a sufficiently white color that the starch need not be bleached prior to use in the tableting formulation, thus eliminating the chlorine-like flavor while still providing a white starch.

In fact, it has been found that the white corn starch of the present invention is whiter than bleached corn starch thereby visually providing even a purer product than the bleached corn starch. Naturally, the white corn starch of the present invention can still be subjected to a bleach step for purposes of microbial control. Alternatively, another method such as radiation or microwave treatment can be used to control microbial growth.

Additionally, it has been found that less energy is needed both to compress the tablet and to eject the tablet from the press compared to either bleached common corn starch or carboxymethyl-cellulose. The lower energy requirement means a cost saving to the tablet manufacturer.

Less energy to form a tablet of a given hardness also means that if the same amount of energy is used to form the tablet with white corn starch, that a stronger tablet is formed. Thus, white corn starch is a more effective binder than conventional bleached corn starch.

Broadly, the present invention can be characterized as an improvement in a process for making pharmaceutical tablets wherein compression force is used to form the pharmaceutical tablets and wherein starch granules are used as a binder and/or filler in formulating the tablets, the improvement comprising using a white starch as a disintegrant/binder. The starch granule used in the present invention is suitably obtained from white common corn and white waxy corn.

Sources of starch for use in the present invention include maize, sorghum, and wheat. The preferred source is a common or a waxy starch which is homozygous in the white recessive gene; more preferred is white common corn starch The white gene is reported to be located on chromosome 6 of maize. See "Development Genetics", Volume 5, pages 1-25, 1984.

Generally, to obtain a starch bearing plant which is homozygous in the recessive mutant gene white (w), a plant with the white gene is crossed with a plant that also has the recessive white gene to obtain some offspring that are homozygous in the white recessive gene. After the homozygous ww genotype is obtained, standard plant breeding techniques are employed to obtain hybrid vigor. Hybrids are preferred because of their high starch yields compared to inbred lines. The methods of crossing plants and of obtaining specific genotypes in the offspring, as well as breeding to obtain hybrid vigor are well-known. The term white starch as used in the specification and claims means a starch extracted from a plant that is homozygous in the recessive white gene or its equivalent. The term white corn starch means that the plant is maize.

The starch from maize being homozygous in the recessive gene white is extracted from the corn kernel in a known manner. Good results have been obtained with a wet milling operation.

The amount of starch of the present invention used in a tablet is an effective amount in order to make the tablet friable. The amount of starch of the present invention employed in a tablet in accordance with the present invention varies from formulation to formulation and depends on a number of factors such as size of tablet and the drug used in the tablet. Good results have been obtained by employing about 5% by weight tablet of white corn starch wherein the maize plant is homozygous in the white recessive gene. The white starch of the present invention can be used in both dry tableting formulations and in wet granulations.

These and other aspects of the present invention may be more fully understood by reference to the following examples:

EXAMPLE 1

This example illustrates the friability of tablets made in accordance with the present invention compared to tablets made with conventional disintegrants/binders. Table I below lists the other disintegrants/binders and the results of the friability tests:

TABLE I

| Disintegrant/Binder | Friability (%) |
|---|---|
| 1. White Common Corn Starch | 0.536 |
| 2. Bleached Common Corn Starch - A | 0.706 |
| 3. Bleached Common Corn Starch - B | 0.521 |
| 4. Microcrystalline Cellulose | 0.611 |

The white common corn starch was obtained from maize and was homozygous in the white recessive gene. Bleached common corn starch-A and bleached common corn starch-B are commercial brands of bleached common corn starch sold under the name Tablet White by American Maize-Products Company of Hammond, Ind.; and PURITY 21 by National Starch and Chemical Corporation of Bridgewater, N.J. The microcrystalline cellulose was a commercial brand sold under the mark AVICEL PH 101. The friability of these tablets was measured using a Roche Friabulator (Erweka) Model TA3, operated at 26 rpm for 4.5 minutes. The machine operates by tumbling 30 tablets and then measuring the loss of weight of the tablet due to the abrasion of the tablets against each other.

These tests demonstrate that the tablets made in accordance with the present invention are comparable to tablets made with conventional disintegration agents/fillers. Thus, the corn starch which is homozygous in the recessive white gene acts as a good binder in the tablets.

The tablets were made in accordance with the formulation listed in Table II.

TABLE II

| Disintegrant/Binder | Amount (mg/250 mg Tablet) | |
|---|---|---|
| Hydrochlorothiazide | 25.0 | (10%) |
| Starch | 12.5 | (5%) |
| Magnesium Sterate | 1.2 | (0.5%) |
| Hydrous Lactose | 211.2 | (84.5%) |
| Distilled Water | 0.03 mg | (.01%) |

In order to make the tablet, the hydrochlorothiazide, lactose and starch were dry mixed in a kitchen aid mixer for five minutes. Then water was added and the mixing continued for thirty seconds. The final mix was then sieve granulated through a 6 mesh screen and dried in an oven to a moisture level of 0.1% by weight. The dried granules were then put through a 14 mesh screen and the magnesium sterate of 40 mesh size was added and mixed in a Turbula mixer for three minutes.

This final mix was compacted with a Stokes B-2 rotary tablet press equipped with a ⅜ inch flat-face punch to a hardness of 6–8 kg and a weight of 250 mg.

EXAMPLE 2

This example illustrates the disintegration time for a tablet made in accordance with the present invention compared to tablets made with the conventional disintegrants/binders. Using the same binders/disintegrants of Example 1. Table III below details the results of the tests.

TABLE III

| Disintegrant/Binder | Disintegration Time (minutes) |
|---|---|
| 1. White Common Corn Starch | 0.58 |
| 2. Bleached Common Corn Starch - A | 0.50 |
| 3. Bleached Common Corn Starch - B | 0.57 |
| 4. Microcrystalline Cellulose | 2.16 |

The tablets were made in accordance with Example 1 above.

Disintegration time was measured in accordance < > with U.S. Pharmaceutical XXII Disintegration Test 701 using the procedure for uncoated tablets in water at 35±2° C. The time listed in Table III is the amount for the tablets to disintegrate completely. The results show that the starch of the present invention is comparable to conventional disintegrants/binders.

EXAMPLE 3

This example illustrates the improved whiteness which is obtained through use of the starch of the present invention compared to other conventional disintegrants/binders. Table IV below illustrates the whiteness value for the starch of the present invention compared to bleached and unbleached common corn starch and microcrystalline cellulose.

TABLE IV

| Disinteqrant/Binder | Hunter Nos. |
|---|---|
| 1. Common Corn ww | 90–96 |
| 2. Common Corn bleached | 90–93 |
| 3. Common Corn unbleached | 65–70 |
| 4. Microcrystalline Cellulose | 57.9 |

The Hunter numbers were obtained using a Hunter Lab Optical Sensor Model D25 on the dry powders using the instrument in accordance with its operating manual. The unbleached common corn starch is a conventional common corn starch sold by American Maize-Products Co. The microcrystalline cellulose is sold under the name AVICEL RC 581 and is a food grade product.

EXAMPLE 4

This example illustrates that less force is needed both to compress a tablet as well as to eject a tablet from a press where the tablet is made with the starch of the present invention compared to other conventional disintegrants/binders. Table V below illustrates the amount of force necessary for compression and ejection. The disintegrants/binders are those of Example 1.

TABLE V

| Disintegrant/Binder | Mean Compression Force (kN) | Mean Ejection Force (N) |
|---|---|---|
| 1. White Common Corn Starch | 18.35 | 365.6 |
| 2. Bleached Common Corn Starch - A | 19.60 | 405.1 |
| 3. Bleached Common Corn Starch - B | 23.46 | 540.9 |

TABLE V-continued

| Disintegrant/Binder | Mean Compression Force (kN) | Mean Ejection Force (N) |
|---|---|---|
| 4. Microcrystalline Cellulose | 20.18 | 495.9 |

These results demonstrate that it took less energy to make the tablets in accordance with the present invention compared to conventional tablets. Table V lists the mean compression force required to produce tablets of the same degree of hardness, approximately 6 kg. These compression force and ejection force measurements were made using conventional equipment in a conventional manner.

It will be understood that the claims are intended to cover all changes and modifications of the preferred embodiments of the invention herein chosen for the purpose of illustration which do not constitute a departure from the spirit and scope of the invention.

What is claimed is:

1. In a process for making pharmaceutical tablets wherein compression is used to form the pharmaceutical tablets and wherein starch is used as a binder in formulating the tablets, the improvement which comprises using an effective amount of a white corn starch obtained from a starch bearing plant which is homozygous with the white gene (ww) as a binder in formulating the tablets thereby reducing the amount of energy necessary to eject the tablets compared to bleached common corn starch and microcellulose, the amount of said starch being effective to make the tablets friable.

2. The process of claim 1 wherein the starch granule is obtained from white common corn.

3. The process of claim 1 wherein the starch granule is obtained from white waxy corn.

4. The process of claim 1 wherein the amount of white starch is about 5% by weight of tablet.

5. The process of claim 2 wherein the amount of white starch is about 5% by weight of tablet.

6. The process of claim 3 wherein the amount of white starch is about 5% by weight of tablet.

* * * * *